United States Patent
Lee et al.

(10) Patent No.: US 9,993,308 B2
(45) Date of Patent: Jun. 12, 2018

(54) TUBE CONTINUUM ROBOT HAVING A TUBE BODY CAPABLE OF LINEAR CONTROL AND ROBOT SYSTEM FOR OPERATION USING THEREOF

(71) Applicant: KOREA INSTITUTE OF SCIENCE AND TECHNOLOGY, Seoul (KR)

(72) Inventors: Woosub Lee, Seoul (KR); Sung Chul Kang, Seoul (KR); Dong-Eun Choi, Seoul (KR); Keri Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 393 days.

(21) Appl. No.: 14/963,643

(22) Filed: Dec. 9, 2015

(65) Prior Publication Data
US 2016/0374765 A1    Dec. 29, 2016

(30) Foreign Application Priority Data
Jun. 23, 2015    (KR) ........................ 10-2015-0088921

(51) Int. Cl.
*A61B 34/30*    (2016.01)
*A61B 17/00*    (2006.01)

(52) U.S. Cl.
CPC .... *A61B 34/30* (2016.02); *A61B 2017/00309* (2013.01); *A61B 2017/00331* (2013.01); *A61B 2017/00991* (2013.01); *A61B 2034/301* (2016.02); *A61B 2034/305* (2016.02)

(58) Field of Classification Search
CPC .............. A61B 2034/301; A61B 34/30; A61B 2034/305; A61B 2017/00991
See application file for complete search history.

(56) References Cited

U.S. PATENT DOCUMENTS

| | | | |
|---|---|---|---|
| 8,578,810 B2 * | 11/2013 | Donhowe ............... | A61B 17/00 600/141 |
| 8,939,963 B2 * | 1/2015 | Rogers ................... | A61B 17/29 227/176.1 |
| 9,895,163 B2 * | 2/2018 | Trovato ............ | A61M 25/0105 |

(Continued)

FOREIGN PATENT DOCUMENTS

| | | |
|---|---|---|
| JP | 2009-515657 A | 4/2009 |
| KR | 10-2009-0019908 A | 2/2009 |

(Continued)

OTHER PUBLICATIONS

Webster III, Robert J., Joseph M. Romano, and Noah J. Cowan. "Mechanics of Precurved-Tube Continuum Robots." Robotics, IEEE Transactions on 25.1 (2009): 67-78, Seoul, Republic of Korea.

*Primary Examiner* — David M Fenstermacher
(74) *Attorney, Agent, or Firm* — NSIP Law

(57) ABSTRACT

The present disclosure relates to a tube continuum robot and a robot system for operation using the same, and the tube continuum robot includes a basic tube body including a basic straight section extending straight, and a basic curved section extending in front of the basic straight section and bent to a predetermined curvature, and a connection tube body having a connection flexible section which is flexibly bendable, the connection tube body formed to be inserted into the basic tube body or to surround an exterior of the basic tube body, the connection tube body being connected to the basic tube body.

18 Claims, 11 Drawing Sheets

(56) References Cited

U.S. PATENT DOCUMENTS

| | | | | |
|---|---|---|---|---|
| 2009/0171271 A1* | 7/2009 | Webster | ............ | A61B 17/3417 604/95.01 |
| 2009/0248045 A1* | 10/2009 | Trovato | ............ | A61B 17/3421 606/130 |
| 2011/0207999 A1* | 8/2011 | Torisawa | ........... | A61B 1/00078 600/114 |
| 2013/0018303 A1 | 1/2013 | Webster et al. | | |
| 2014/0094782 A1 | 4/2014 | Jeong et al. | | |
| 2016/0151908 A1* | 6/2016 | Woodley | ............ | A61B 1/0053 74/490.04 |

FOREIGN PATENT DOCUMENTS

| | | |
|---|---|---|
| KR | 10-1173619 B1 | 8/2012 |
| KR | 10-2012-0102049 A | 9/2012 |
| KR | 10-2012-0111346 A | 10/2012 |
| KR | 10-1280065 B1 | 6/2013 |
| KR | 10-1466705 B1 | 12/2014 |
| WO | WO 2007/059233 A2 | 5/2007 |
| WO | WO 2007-146987 A2 | 12/2007 |
| WO | WO 2011/060042 A1 | 5/2011 |

* cited by examiner

TUBE CONTINUUM ROBOT HAVING A TUBE BODY CAPABLE OF LINEAR CONTROL AND ROBOT SYSTEM FOR OPERATION USING THEREOF

CROSS-REFERENCE TO RELATED APPLICATION

This application claims priority to Korean Patent Application No. 10-2015-0088921, filed on Jun. 23, 2015, and all the benefits accruing therefrom under 35 U.S.C. § 119, the contents of which in its entirety are herein incorporated by reference.

BACKGROUND

1. Field

The present disclosure relates to a tube continuum robot having a tube body capable of linear control and a robot system for operation using the tube continuum, and more particularly, a tube continuum robot for performing a predetermined task by inserting a plurality of tube continua into a long cannula path and a robot system for operation using the same.

2. Description of the Related Art

A cannula insertion device is used to perform a predetermined task by inserting a long hollow tube continuum into a narrow space, and typically includes, for example, equipment for microsurgery in use for minimally invasive surgery.

Minimally invasive surgery refers to surgery that can be done through minimal incision instead of open surgery, and has advantages of less scarring or after-effects and quick recovery due to a small incision.

As equipment for microsurgery in use for minimally invasive surgery should perform a predetermined task such as an operation within a narrow space, many studies on production and control of such equipment are being made.

Traditional equipment for microsurgery is made from an ultra elastic shape memory alloy having a curvature. The equipment performs a predetermined task by moving different tube bodies that make up the tube continuum having a diameter and a curvature in a state that the tube bodies overlap each other. Also, the equipment can control a location of an end-effector based on an input angle by the interaction between the tube bodies.

According to the related art, a final location of the end-effector is estimated through a resulting angle at which the overlapping tube bodies have minimum energy by using an energy equation.

Specifically, each of the tube bodies can be rotated or moved back and forth independently of each other. By suitably rotating and/or translating each of the tube bodies, each of the tube bodies may be suitably bent to conform to the shape of the space into which the equipment is inserted, and finally, the end-effector may be placed in a desired location.

However, the related art has a disadvantage of a complex equation in the calculation for location control of the end-effector because the location of the end-effector should be controlled in consideration of an interference relationship between the plurality of tube bodies.

Also, according to the related art, as the plurality of tubes is arranged such that the tubes are inserted into each other or surrounded by each other, a curved area having a predetermined curvature is formed between each of the tubes. Thus, an interference phenomenon between the plurality of tubes takes place in the curved area, and as a result, the end-effector is not placed in a desired location.

Also, when a plurality of tube continua is inserted into the long cannula path where an operation is conducted, an interference phenomenon between the tube continua occurs, and as a result, the end-effector is not accurately placed in a desired location.

Also, when a plurality of tube continua is inserted into the cannula path, a congestion phenomenon occurs at an end part of each tube continuum consisting of the plurality of tube bodies. Thus, when inserting a plurality of tube continua into the cannula path, it is necessary to increase an entrance width of the cannula path while considering such a congestion phenomenon.

RELATED LITERATURES

US Patent Publication No. 2013/0018303

SUMMARY

To solve the problem of the related art, the present disclosure is directed to providing a tube continuum robot that may effectively adjust the orientation of an end-effector connected to a front end of a micro tube body by deriving an equation in the calculation for controlling the location of the micro tube body as a simple linear equation, and a robot system for operation that may prevent a congestion phenomenon occurring between a plurality of tube continua when the plurality of tube continua is inserted into a cannula path and minimize an entrance diameter of the cannula path.

To solve the object, a tube continuum robot according to the present disclosure includes a basic tube body including a basic straight section extending straight, and a basic curved section extending in front of the basic straight section and bent to a predetermined curvature, and a connection tube body having a connection flexible section which is flexibly bendable, the connection tube body formed to be inserted into the basic tube body or to surround an exterior of the basic tube body, the connection tube body being connected with the basic tube body, wherein the connection flexible section has a length longer than or equal to a length of the basic curved section, when the basic tube body and the connection tube body are connected, the connection flexible section is placed to fully cover the basic curved section so that at least a part of the connection flexible section is bent to conform to a shape of the basic curved section, a front end of the connection tube body is placed at a more anterior location than a front end of the basic tube body, and a location and an orientation of the front end of the connection tube body is adjustable by relatively moving back and forth or rotating the basic tube body and the connection tube body.

The connection tube body may include an outer side connection tube body formed to surround the exterior of the basic tube body, the outer side connection tube body having an outer side connection flexible section which is placed to fully cover the basic curved section and bent to conform to the shape of the basic curved section, and an inner side connection tube body formed to be inserted into the basic tube body, the inner side connection tube body having an inner side connection flexible section which is placed to fully cover the basic curved section and bent to conform to the shape of the basic curved section, and each of the basic tube body, the inner side connection tube body, and the outer side connection tube body may be moveable back and forth or rotatable independently.

The front end of the outer side connection tube body may be placed at a more anterior location than the front end of the basic tube body, the front end of the inner side connection tube body may be placed at a more anterior location than the front end of the outer side connection tube body, and the location and orientation of the front end of the inner side connection tube body may be adjusted by relatively moving back and forth or rotating each of the basic tube body, the inner side connection tube body, and the outer side connection tube body.

A basic flexible section which is flexibly bendable may be formed in a part or the whole of the basic tube body, and a basic guide section made from metal may be installed on an outer surface of the basic flexible section at an area of overlap with the connection flexible section.

The outer side connection tube body may include an outer side straight section extending straight, and an outer side curved section extending in front of the outer side straight section and bent to a predetermined curvature, and the outer side curved section may be placed at a more anterior location than the basic curved section and does not cover the basic curved section.

The outer side connection flexible section may be formed in a part or the whole of the outer side curved section, and a connection guide section made from metal may be installed on an outer surface of the outer side curved section having the outer side connection flexible section.

The inner side connection flexible section may be formed with a length to cover both the basic curved section and the outer side curved section.

The inner side connection flexible section may include a first inner side connection flexible section formed to cover the basic curved section, and a second inner side connection flexible section formed to cover the outer side curved section.

The inner side connection tube body may include an inner side straight section extending straight, and an inner side curved section extending in front of the inner side straight section and bent to a predetermined curvature, and the inner side curved section may be placed at a more anterior location than the outer side curved section and does not cover the outer side curved section.

An end-effector may be formed at the front end of the inner side connection tube body to perform a task within a task space into which the inner side connection tube body is inserted.

The basic tube body may further include a basic extension section extending straight in front of the basic curved section, and the outer side connection tube body may further include an outer side extension section extending straight in front of the outer side curved section.

Also, a robot system for operation using the tube continuum robot includes a plurality of tube continua, each tube continuum including an undeformed section extending straight, and a deformed section extending in front of the undeformed section and having a plurality of curved sections, wherein each deformed section of the plurality of tube continua is formed with a spiral structure and controllable to minimize a width of the plurality of tube continua, the plurality of tube continua enters along an entry passage in a state that the undeformed sections are arranged in parallel while the deformed sections are twisted with each other by their rotation and extension in the same direction, and when the plurality of tube continua is moved to a task space having a wider volume than the entry passage, location of ends of the deformed sections is controlled.

The location of the ends of the deformed sections may be controlled by moving back and forth or rotating each of the plurality of tube continua independently of each other.

The deformed section may include a basic curved section respectively extending in front of the undeformed section and bent to a predetermined curvature and a connection tube body having a connection flexible section which is flexibly bendable, the connection tube body formed to be inserted into the basic curved section or to surround an exterior of the basic curved section, and a basic tube body composed of the undeformed section and the basic curved section may be moveable back and forth or rotatable independently of the connection tube body.

The connection tube body may include an outer side connection tube body having an outer side connection flexible section which is formed to surround the exterior of the basic curved section, placed to overlap with the basic curved section, and bent to conform to a shape of the basic curved section, and an inner side connection tube body having an inner side connection flexible section which is formed to be inserted into the basic curved section, placed to overlap with the basic curved section, and bent to conform to the shape of the basic curved section, and each of the inner side connection tube body and the outer side connection tube body may be moveable back and forth or rotatable independently.

The outer side connection tube body may include an outer side straight section extending straight, and an outer side curved section extending in front of the outer side straight section and bent to a predetermined curvature, the inner side connection tube body may include an inner side straight section extending straight, and an inner side curved section extending in front of the inner side straight section and bent to a predetermined curvature, and when the plurality of tube continua is moved to the task space, at least one of the basic curved section, the outer side curved section, and the inner side curved section may be rotated.

A front end of the outer side connection tube body may be placed at a more anterior location than a front end of the basic tube body, a front end of the inner side connection tube body may be placed at a more anterior location than the front end of the basic tube body and a front end of the outer side connection tube body, and the tube continuum may further include a wire made from a flexibly bendable material, the wire being inserted into the inner side connection tube body.

A gap extending along a lengthwise direction of the entry passage may be formed between the plurality of continua, and a camera extending straight along the lengthwise direction of the entry passage may be inserted into the gap.

DETAILED DESCRIPTION

Figure 1:
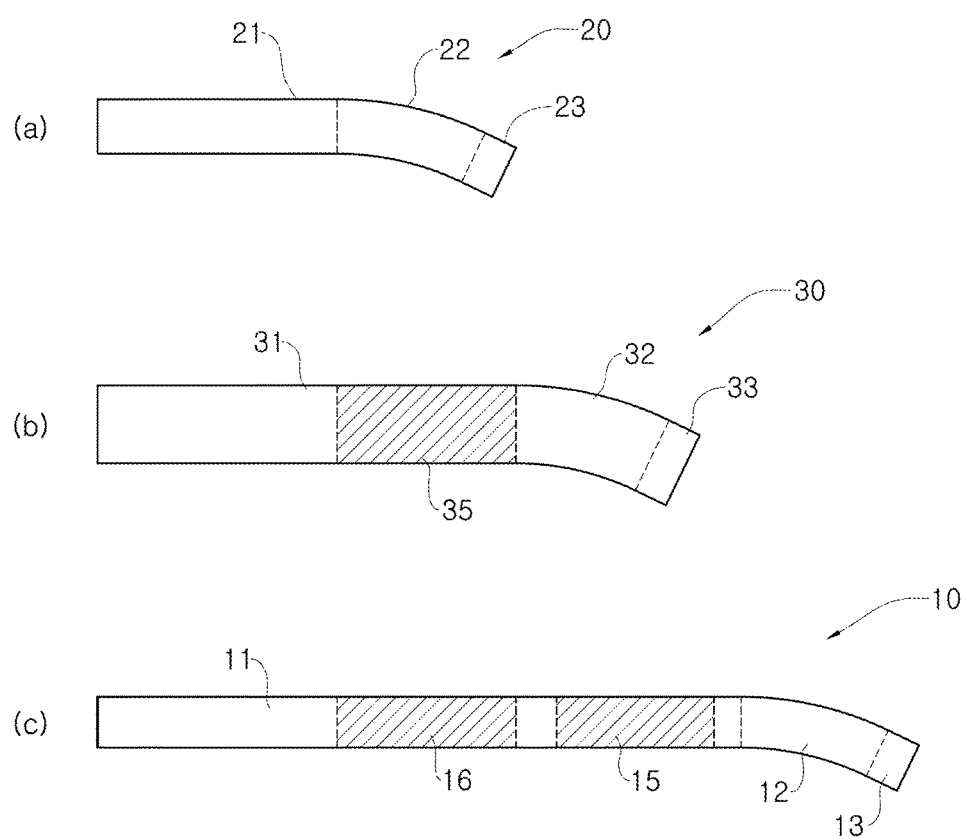
FIG. 1 is a diagram showing the shape of each tube body according to an embodiment of the present disclosure.

Hereinafter, preferred embodiments of the present disclosure will be described with reference to the accompanying drawings. The present disclosure is described with reference to the embodiments shown in the drawings, but it is described as one example only and the technical features and key elements and their operation of the present disclosure are not limited thereby.

Figure 2:
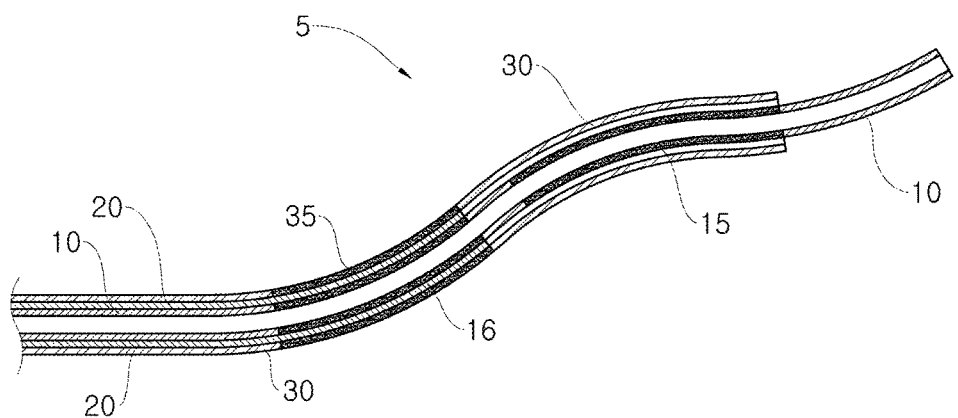
FIG. 2 is a cross-sectional view showing a tube continuum in which the tube bodies are combined.

FIG. 1 is a diagram showing the shape of each tube body according to an embodiment of the present disclosure, and FIG. 2 is a cross-sectional view showing that the tube bodies are combined.

Referring to FIGS. 1 and 2, a tube continuum 5 according to this embodiment includes a plurality of tube bodies 10, 20, and 30 having different diameters. The plurality of tube bodies includes an outer side connection tube body 30 placed at the outermost side and having a larger diameter than the other tube bodies, an inner side connection tube body 10 inserted into the outer side connection tube body 30 and having a smaller diameter than the other tube bodies, and a basic tube body 20 placed between the outer side connection tube body 30 and the inner side connection tube body 10.

That is, the basic tube body 20 is configured to be inserted into the outer side connection tube body 30 and surround the inner side connection tube body 10.

The basic tube body 20 includes a basic straight section 21 extending straight, and a basic curved section 22 extending in front of the basic straight section 21 and bent to a predetermined curvature.

The outer side connection tube body 30 includes an outer side straight section 31 extending straight, and an outer side curved section 32 extending in front of the outer side straight section 31 and bent to a predetermined curvature.

Likewise, the inner side connection tube body 10 includes an inner side straight section 11 extending straight, and an inner side curved section 12 extending in front of the inner side straight section 11 and bent to a predetermined curvature.

The tube bodies 10, 20, and 30 have such a location relationship in which the tube bodies are inserted into each other or surrounded by each other. Thus, extension sections 13, 23, and 33 extending straight in front of the curved sections 12, 22, and 32 may be respectively connected to the ends of the curved sections 12, 22, and 32.

Specifically, the basic tube body 20 may further include a basic extension section 23 extending straight in front of the basic curved section 22. Likewise, the outer side connection tube body 30 may further include an outer side extension section 33 extending straight in front of the outer side curved section 32, and the inner side connection tube body 10 may further include an inner side extension section 13 extending straight in front of the inner side curved section 12.

Each of the extension sections 13, 23, and 33 may act as an adjuster to place each of the tube bodies 10, 20, and 30 in a right location when combining the tube bodies 10, 20, and 30.

The outer side connection tube body 30 has an outer side connection flexible section 35 which is placed to fully cover the basic curved section 22 and bent to conform to the shape of the basic curved section 22.

The term "fully cover" as used herein means that a first element longer than a second element then covers the full length of the second element against an inner or outer side along a lengthwise direction of a tube body.

That is, the outer side connection flexible section 35 is longer than the basic curved section 22 and covers the basic curved section 22 against the outer side throughout the entire length of the basic curved section 22 along the lengthwise direction of the tube body.

If the outer side connection flexible section 35 is longer than the basic curved section 22, the outer side connection flexible section 35 fully covers the basic curved section 22 while fully or partially covering the basic straight section 21 and/or the basic extension section 23.

The term "partially cover" as used herein should be construed as a first element covering a second element against an inner or outer side over only part of the length of the second element along a lengthwise direction of a tube body.

The inner side connection tube body 10 includes a first inner side connection flexible section 16 which is placed to fully cover the basic curved section 22 and bent to conform to the shape of the basic curved section 22, and a second inner side connection flexible section 15 which is placed to fully cover the outer side curved section 32 and bent to conform to the shape of the outer side curved section 32.

That is, the first inner side connection flexible section 16 is longer than the basic curved section 22 and covers the basic curved section 22 against the inner side throughout the entire length of the basic curved section 22 along the lengthwise direction of the tube body. Likewise, the second inner side connection flexible section 15 is longer than the outer side curved section 32 and covers the outer side curved section 32 against the inner side throughout the entire length of the outer side curved section 32 along the lengthwise direction of the tube body.

A front end of the outer side connection tube body 30 is placed at a more anterior location than a front end of the basic tube body 20. Specifically, with respect to a cannula insertion device, a length of the outer side connection tube body 30 protruding outside is longer than a length of the basic tube body 20 protruding outside.

Likewise, a front end of the inner side connection tube body 10 is placed at a more anterior location than a front end of the outer side connection tube body 30. Specifically, with respect to a cannula insertion device, a length of the inner side connection tube body 10 protruding outside is longer than a length of the outer side connection tube body 30 protruding outside.

That is, a front end of the inner side connection tube body 10 is placed at a more anterior location than a front end of the outer side connection tube body 30 and a front end of the basic tube body 20. Thus, an end-effector 1100 is formed at the front end of the inner side connection tube body 10 to perform a task within a task space into which the inner side connection tube body 10 is inserted.

Also, the basic tube body 20 and each of the connection tube bodies 10 and 30 are moveable back and forth or rotatable independently of each other. Thus, the location of the end-effector 1100 may be controlled by rotating or moving each of the tube bodies 10, 20, and 30 back and forth independently of each other.

For independent operation of the outer side connection tube body 30 and the basic tube body 20, the outer side curved section 32 is placed at a more anterior location than the basic curved section 22 and does not cover the basic curved section 22.

The term "not cover" as used herein should be construed as a first element and a second element not overlapping each other with respect to a lengthwise direction of a tube body.

Likewise, for independent operation of the inner side connection tube body 10, the basic tube body 20 and the outer side connection tube body 30, the inner side curved section 12 is placed at a more anterior location than the outer side curved section 32 and the basic curved section 22 and does not cover the outer side curved section 32 and the basic curved section 22.

Each of the tube bodies 10, 20, and 30 is made from a stiff material. However, as described in the foregoing, the outer side connection tube body 30 has the outer side connection flexible section 35 having a predetermined elasticity, and the inner side connection tube body 10 has the first inner side connection flexible section 16 and the second inner side connection flexible section 15 having a predetermined elasticity.

The outer side connection flexible section 35 and the first inner side connection flexible section 16 fully covers the basic curved section 22, and the second inner side connection flexible section 15 fully covers the outer side curved section 32. Thus, an interference phenomenon between the tube bodies does not occur at the curved sections of each of the tube bodies.

A spacer (not shown) may be installed between the outer side connection tube body 30 and the inner side connection tube body 10 to fix the location of the two elements. Specifically, the spacer (not shown) is placed between an inner surface of the outer side connection tube body 30 and an outer surface of the inner side connection tube body 10 to prevent each of the connection tube bodies 10 and 30 from being twisted or entangled with each other.

Figure 3:
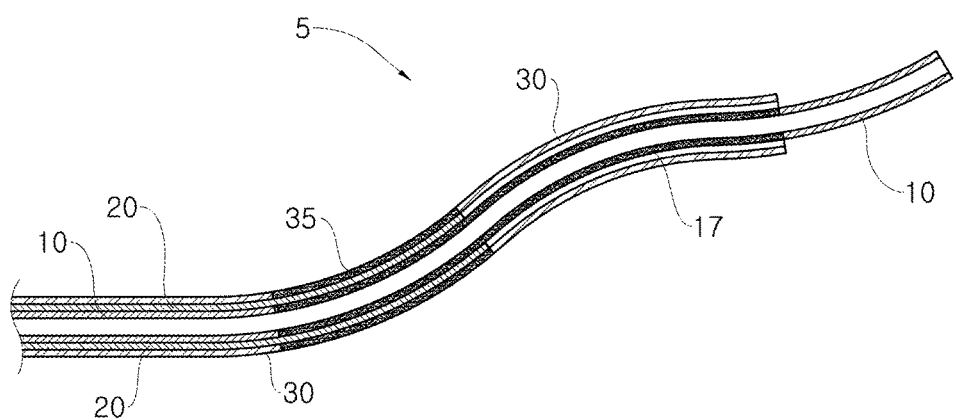
FIG. 3 is a cross-sectional view showing the tube continuum according to another embodiment of the present disclosure.

FIG. 3 shows an embodiment in which the number of connection flexible sections formed in the inner side connection tube body 10 is one.

An inner side connection flexible section 17 according to this embodiment is formed with a length to fully cover both the basic curved section 22 and the outer side curved section 32. As described in the foregoing, the inner side connection flexible section 17 has a predetermined elasticity, and thus changes in shape and is bent to conform to the shape of the basic curved section 22 and the outer side curved section 32.

An interference phenomenon between the tube bodies 10, 20, and 30 occurs at the basic curved section 22 and the outer side curved section 32. However, because the inner side connection flexible section 17 is formed at a region corresponding to the basic curved section 22 and the outer side curved section 32, the occurrence of an interference phenomenon at the curved sections of the tube bodies may be minimized. Accordingly, the location of the tube bodies 10, 20, and 30 may be controlled by a simple linear equation due to the inner side connection flexible section 17.

Figure 4:
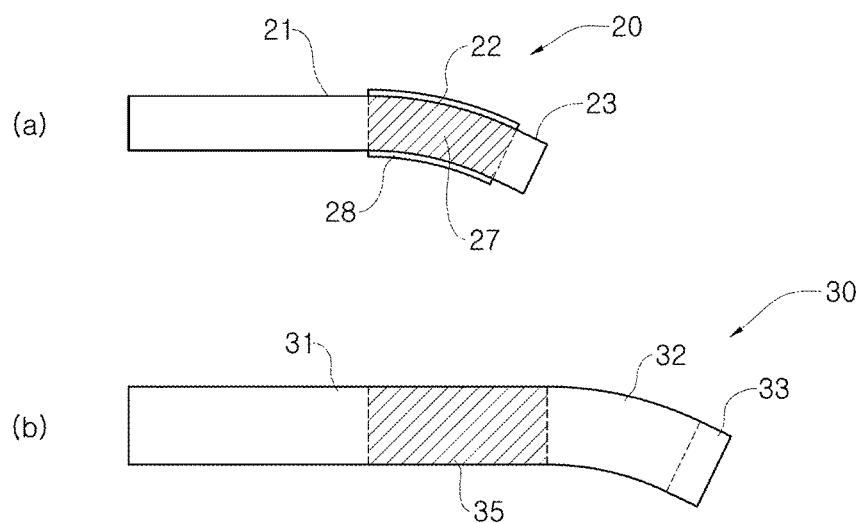
FIG. 4 is a diagram showing the shape of each tube body according to still another embodiment of the present disclosure.
Figure 5:
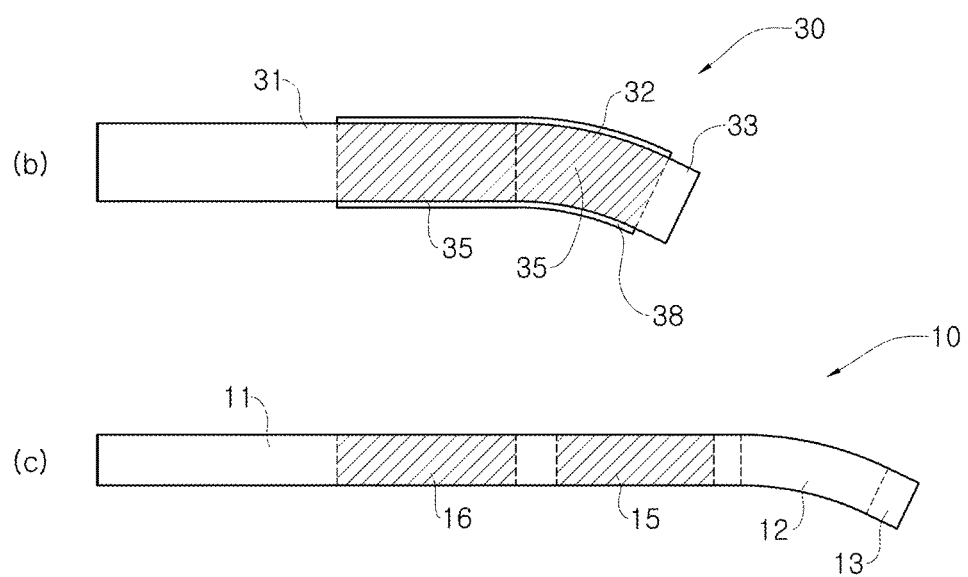
FIG. 5 is a diagram showing another example of the shape of each tube body shown in FIG. 4.

FIG. 4 is a diagram showing the shape of each tube body according to still another embodiment of the present disclosure, and FIG. 5 is a diagram showing another example of the shape of each tube body shown in FIG. 4.

Referring to the drawings, a basic flexible section 27 which is flexibly bendable may be formed in a part or the whole of the basic tube body 20. The basic flexible section 27 may be formed in a part or the whole of the basic straight section 21 or in a part or the whole of the basic curved section 22.

For example, as shown in FIG. 4, the basic flexible section 27 may be formed in the basic curved section 22. In this case, the basic flexible section 27 is placed such that it overlaps with the outer side connection flexible section 35 surrounding the exterior of the basic curved section 22 and the first inner side connection flexible section 16 (or a part of the inner side connection flexible section 17) inserted into the basic curved section 22, causing a problem such as twisting between the flexible sections or a change in angle of a curve. Thus, a basic guide section 28 made from metal may be installed on the outer surface of the basic flexible section 27.

The basic guide section 28 is installed such that it surrounds the outer surface of the basic flexible section 27, so while the shape of the basic curved section 22 is being maintained, the smooth operation control of the tube bodies 10, 20, and 30 may be achieved.

Furthermore, the basic flexible section 27 may be also formed in a part or the whole of the basic straight section 21. In this case, the basic guide section 28 is also installed on the outer surface of the basic flexible section 27, so while the shape of the basic tube body 20 is being maintained, the operation control of the tube bodies 10, 20, and 30 may be achieved.

As another example, as shown in FIG. 5, the outer side connection flexible section 35 is not only installed at a location corresponding to the basic curved section 22, but also may be formed in a part or the whole of the outer side curved section 32. In this case, the outer side connection flexible section 35 is placed such that it overlaps with the second inner side connection flexible section 15 (or other part of the inner side connection flexible section 17), causing a problem such as twisting or a change in angle of a curve. Thus, an outer side connection guide section 38 made from metal may be installed on the outer surface of the outer side connection flexible section 35.

The outer side connection guide section 38 is installed such that it surrounds the outer surface of the outer side curved section 32, so while the shape of the outer side curved section 32 is being maintained, the smooth operation control of the tube bodies 10, 20, and 30 may be achieved.

In addition, the outer side connection flexible section 35 may be also installed at any part of the outer side straight section 31 other than a location corresponding to the basic curved section 22. In this case, the outer side connection guide section 38 is also installed on the outer surface of the outer side connection flexible section 35, so while the shape of the outer side connection tube body 30 is being maintained, the operation control of the tube bodies 10, 20, and 30 may be achieved.

In addition, although not shown, the inner side connection tube body 10 may also have an inner side connection flexible section formed at any part other than the inner side connection flexible sections 15, 16, and 17. However, an inner side connection guide section made from metal is preferably installed on the outer surface of the inner side connection flexible section to maintain the overall shape of the inner side connection tube body 10.

Figure 6:
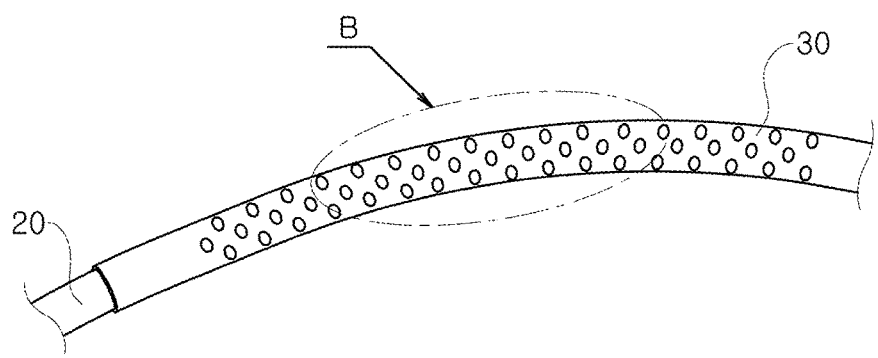
FIG. 6 is a diagram showing the shape of a flexible section according to an embodiment of the present disclosure.
Figure 7:
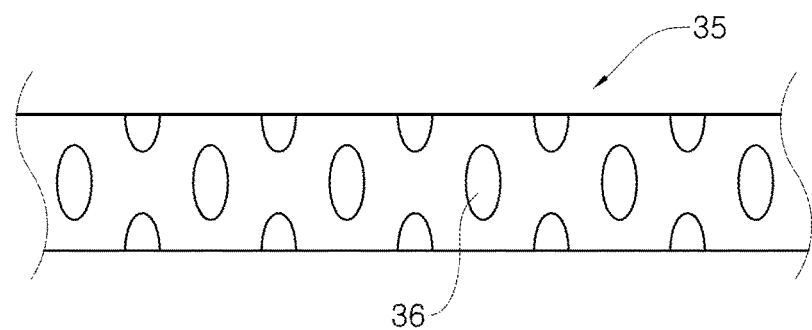
FIG. 7 is an enlarged view of section B in FIG. 6.

FIGS. 6 and 7 show a method of implementing the flexible section according to an embodiment of the present disclosure. This embodiment is described with an example of the outer side connection flexible section 35 formed in the outer side connection tube body 30.

The outer side connection flexible section 35 has a plurality of holes 36. The outer side connection flexible section 35 has a predetermined elasticity by the plurality of holes 36, and accordingly, the outer side connection flexible section 35 is bent to conform to the shape of the basic curved section 22. The plurality of holes 36 may be formed in various shapes. That is, so long as it is possible to provide a predetermined elasticity to the tube bodies 10 and 30, there is no limitation on the number or shape of the holes 36.

Figure 8:
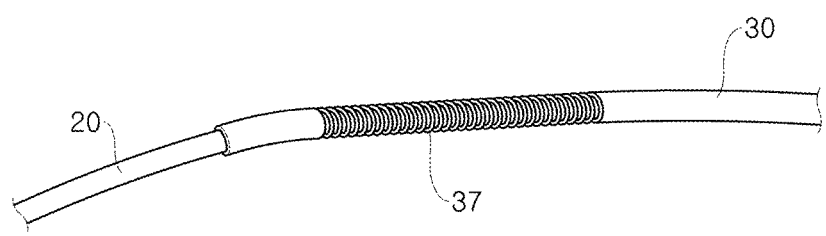
FIG. 8 is a diagram showing the shape of a flexible section according to another embodiment of the present disclosure.

FIG. 8 shows a method of implementing the connection flexible section according to another embodiment of the present disclosure. Similar to the previous embodiment, this embodiment is also described with an example of the outer side connection flexible section 35 formed in the outer side connection tube body 30.

The outer side connection flexible section 35 may be an elastic member 37 having a predetermined elasticity. The elastic member 37 may be formed from a material having elasticity, for example, in the same way as a spring and a coil.

Figure 9:
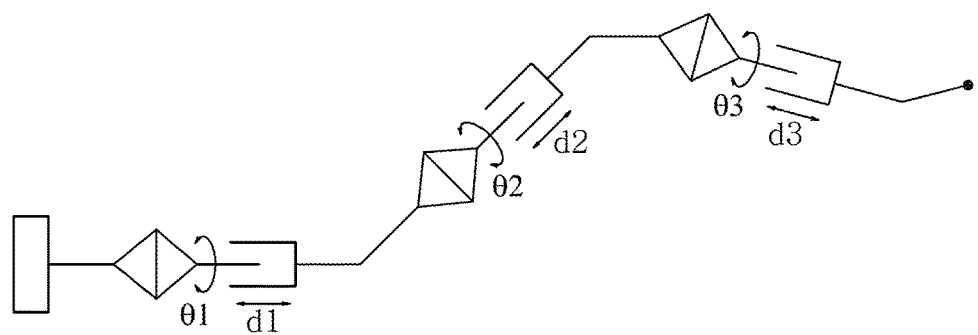
FIG. 9 is a conceptual diagram showing that the location of a tube body can be controlled by a simple linear equation.

FIG. 9 is a conceptual diagram showing that the location of the tube body can be controlled by a simple linear equation.

In this embodiment, each of the tube bodies 10, 20, and 30 rotates or moves back and forth independently of each other. Thus, there are a total of six factors influencing on the movement of the tube bodies 10, 20, and 30; specifically, parameters θ1 and d1 for the rotation and back-and-forth movement of the basic tube body 20, parameters θ2 and d2 for the rotation and back-and-forth movement of the outer side connection tube body 30, and parameters θ3 and d3 for the rotation and back-and-forth movement of the inner side connection tube body 10. That is, the tube bodies 10, 20, and 30 may be disposed at a location desired by a user by moving the tube bodies 10, 20, and 30 independently of each other according to the six parameter values.

Conventionally, a curve region having a predetermined curvature is formed in a plurality of tubes having an arrangement relationship in which the tubes are inserted into each other or surrounded by each other. An interference phenomenon between the plurality of tubes occurs at the curve region, and by this interference phenomenon, there is a problem with a complex equation in the calculation for controlling the location of the tube bodies.

However, according to the present disclosure, because the outer side connection flexible section 35 and the first inner side connection flexible section 16 (or a part of the inner side connection flexible section 17) fully cover the basic curved section 22, and the second inner side connection flexible section 15 (or other part of the inner side connection flexible section 17) fully covers the outer side curved section 32, an interference phenomenon occurring at the curved sections of the tube bodies may be prevented. Thus, the user can control the location of the tube bodies 10, 20, and 30 only by solving a simple linear equation as shown in FIG. 9.

To find the six parameter values, six equations are needed. The equations may be derived from FIG. 10. Specifically, when orientation vectors and location vectors for start points and end points of the curved sections 12, 22, and 32 of each of the tube bodies are calculated, an equation for each point may be derived through the vector values.

Figure 10:
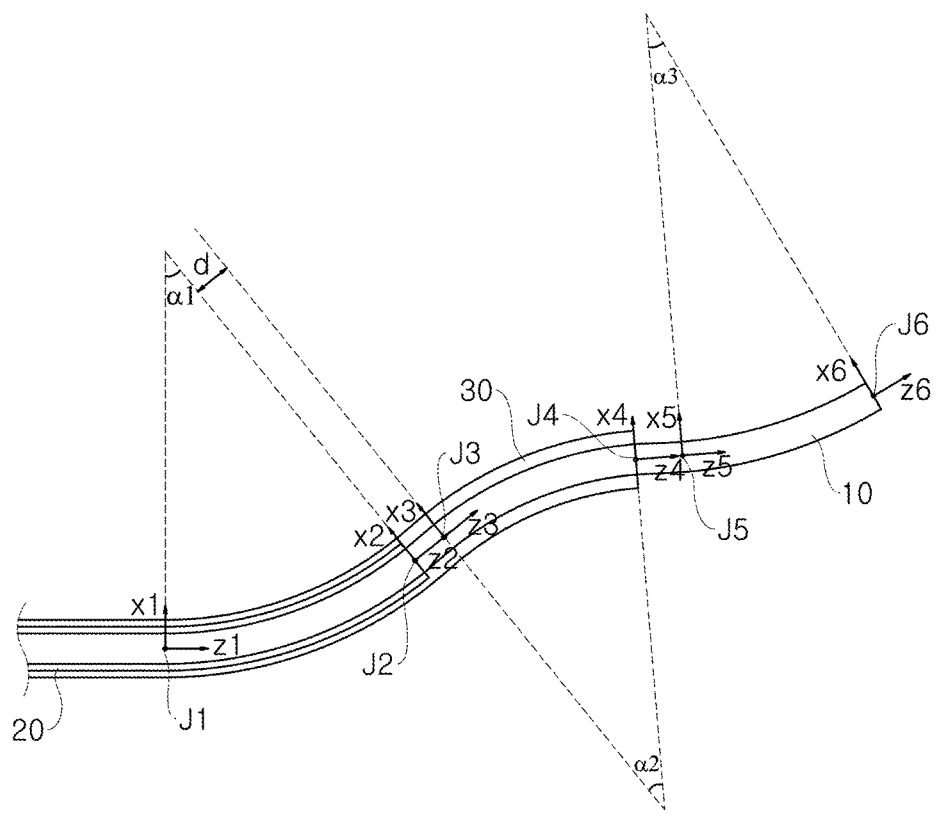
FIG. 10 is a diagram showing a mathematical expression for controlling the location of the tube bodies.

As shown in FIG. 10, the start points of the curved sections 12, 22, and 32 of the tube bodies are designated as a first joint J1, a third joint J3 and a fifth joint J5, the end points of the curved sections 12, 22, and 32 are designated as a second joint J2, a fourth joint J4 and a sixth joint J6.

The orientation vectors and location vectors of the first to sixth joints J1-J6 may be derived through the following table and equations.

TABLE 1

| Type | Orientation vector | Location vector |
|---|---|---|
| First joint (J1) | [0, 0, 1] | q1 |
| Second joint (J2) | [0, 0, 0] | q2 |
| Third joint (J3) | [sin(α1), 0, cos(α1)] | q3 |
| Fourth joint (J4) | [0, 0, 0] | q4 |
| Fifth joint (J5) | [sin(α1-α2), 0, cos(α1-α2)] | q5 |
| Sixth joint (J6) | [0, 0, 0] | q6 |

The values of q1 to q6 may be derived using the following equations.

$$q1=[0, 0, 0]'$$

$$q2=[0, 0, d/2]'$$

$$q3=q2+r_1[1-\cos(\alpha_1), 0, \sin(\alpha_1)]'+d/2[\sin(\alpha_1), 0, \cos(\alpha_1)]'$$

$$q4=[\sin(\alpha_1), 0, \cos(\alpha_1)]'$$

$$q5=q3+2r_2 \sin(\alpha_2/2)[\sin(\alpha_1-\alpha_1/2), 0, \cos(\alpha_1-\alpha_2/2)]'+d[\sin(\alpha_1), 0, \cos(\alpha_1)]'+d/2[\sin(\alpha_1-\alpha_2), 0, \cos(\alpha_1-\alpha_2)]'$$

$$q6=[\sin(\alpha_1-\alpha_2), 0, \cos(\alpha_1-\alpha_2)]'$$

With respect to the xz plane, when a normal line to a tangent line extending in the lengthwise direction of the tube body 5 from the first joint J1 is x1 and a normal line to a tangent line extending in the lengthwise direction of the tube body 5 from the second joint J2 is x2, an angle between the x1 and the x2 is $\alpha_1$. Likewise, with respect to the xz plane, when a normal line to a tangent line extending in the lengthwise direction of the tube body 5 from the third joint J3 is x3 and a normal line to a tangent line extending in the lengthwise direction of the tube body 5 from the fourth joint J4 is x4, an angle between the x3 and the x4 is $\alpha_2$.

Also, the d denotes a distance between the end point of the basic curved section 22 and the start point of the outer side curved section 32.

On substituting the values of $\alpha_1$, $\alpha_2$, and d into the equations, the orientation vectors and location vectors of the first to sixth joints J1-J6 may be derived, and as a result, the tube bodies 10, 20, and 30 may be disposed at a location desired by the user by controlling the rotation or back-and-forth movement of the tube bodies 10, 20, and 30.

Figure 11A:
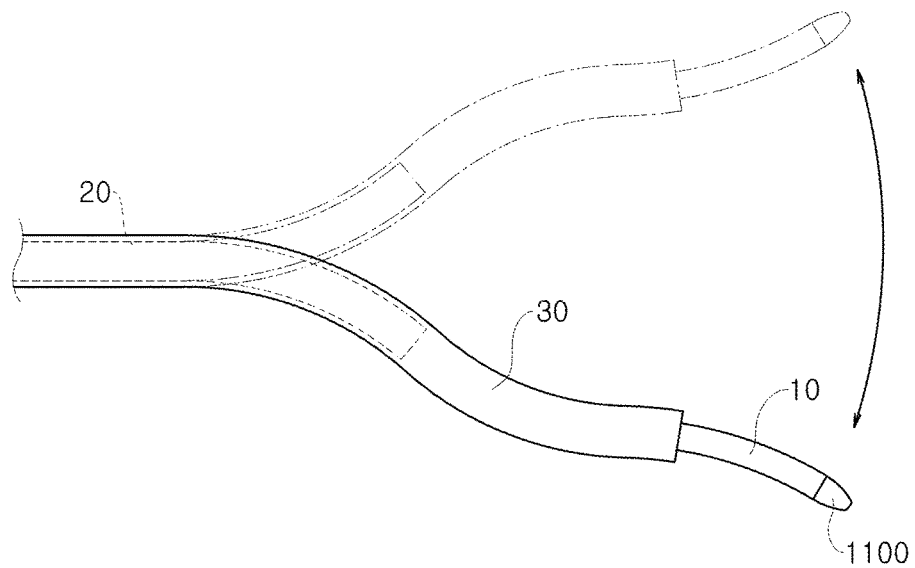
FIG. 11a is a diagram illustrating a rotating movement of the tube body.

Each of the tube bodies 10, 20, and 30 may be rotated or moved back and forth independently of each other. For example, in FIG. 11a, the tube bodies 10, 20, and 30 are rotated 180 degrees. In addition, because the basic tube body 20, the inner side connection tube body 10, and the outer side connection tube body 30 are rotatable independently of each other, the movement range of the end-effector 1100 may be expanded by the rotation of the tube bodies 10, 20, and 30.

Figure 11B:
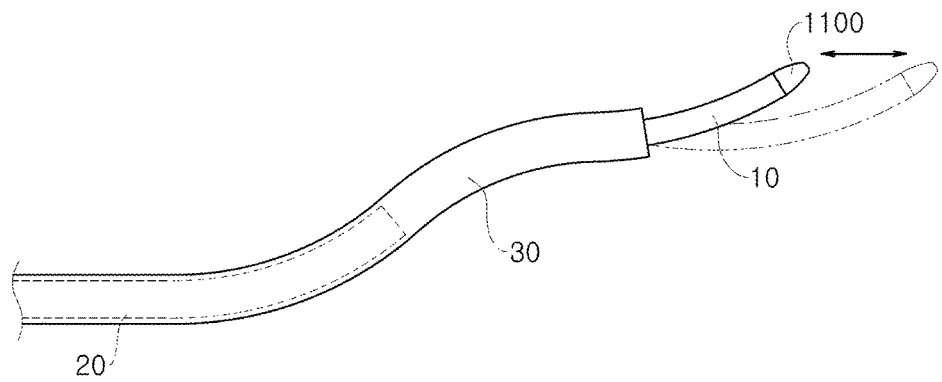
FIG. 11b is a diagram illustrating a back-and-forth movement of the tube body.

FIG. 11b shows that the inner side connection tube body 10 is moved back and forth independently. Although FIG. 11b shows that the inner side connection tube body 10 is moved back and forth independently, it should be noted that the basic tube body 20 and the outer side connection tube body 30 can be also moved back and forth independently. However, the back-and-forth movement of each of the tube bodies 10, 20, and 30 may be only made within the range in which the outer side connection flexible section 35 and the first inner side connection flexible section 16 (or a part of the inner side connection flexible section 17) fully covers the basic curved section 22, and the second inner side connection flexible section 15 (or other part of the inner side connection flexible section 17) fully covers the outer side curved section 32.

Hereinafter, a detailed description of a process in which a plurality of tube continua each consisting of the tube bodies 10, 20, and 30 is simultaneously inserted along an entry passage to perform an operation is provided.

Figure 12:
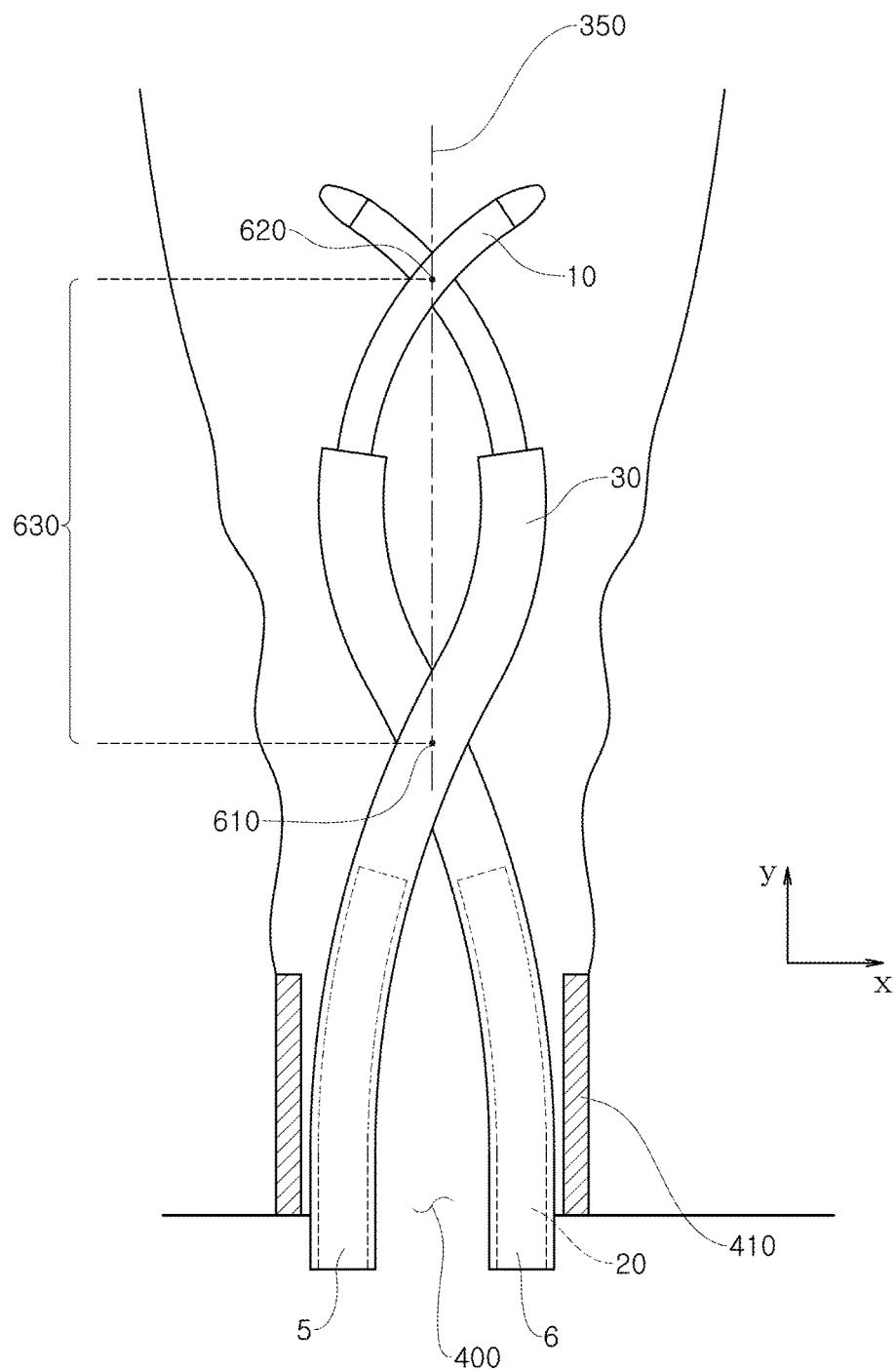
FIG. 12 is a diagram showing a twisted shape of a first tube continuum and a second tube continuum inserted through an entry passage.
Figure 13:
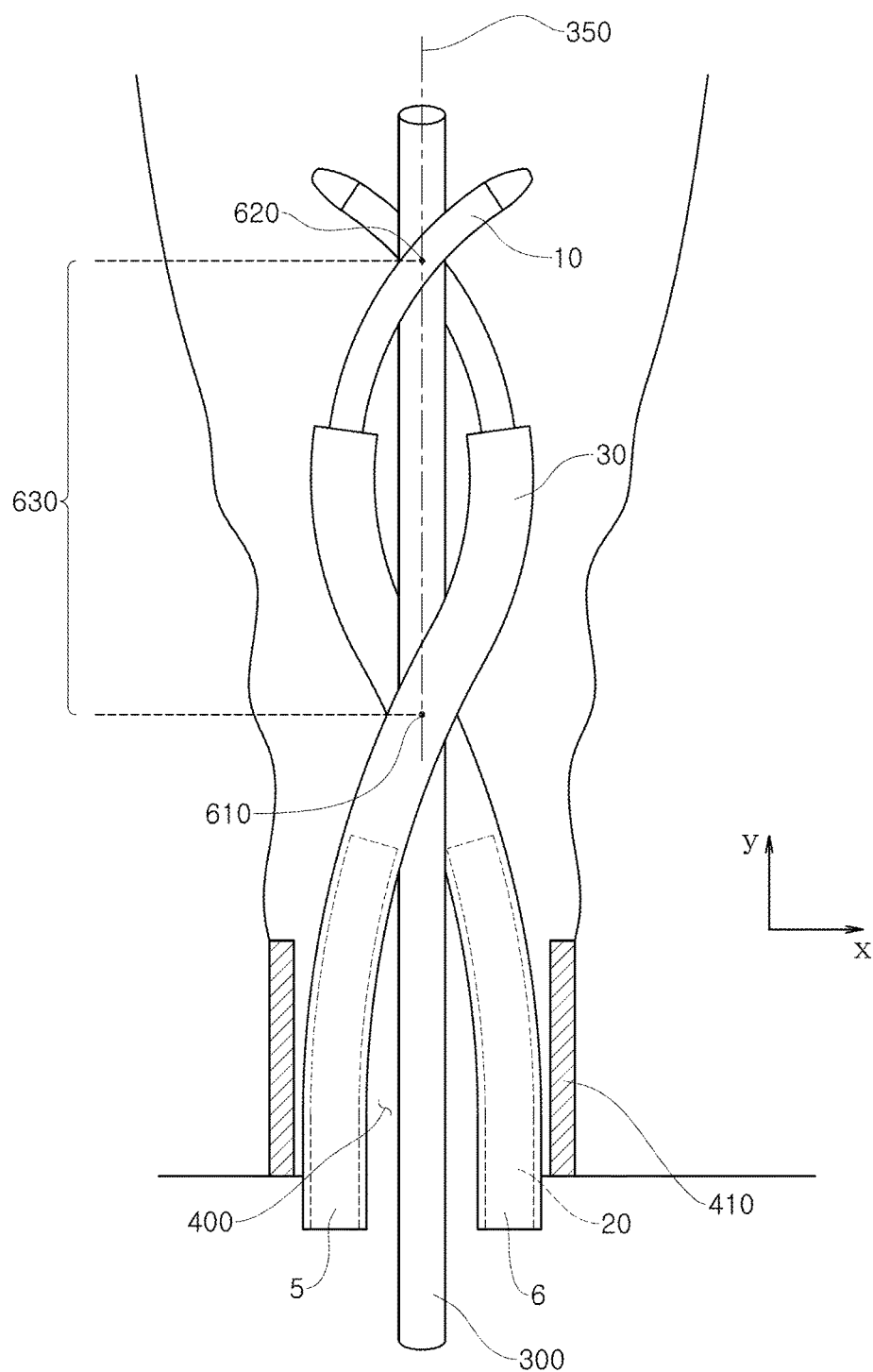
FIG. 13 is a diagram showing that a camera is inserted into a gap formed between the first tube continuum and the second tube continuum.
Figure 14:
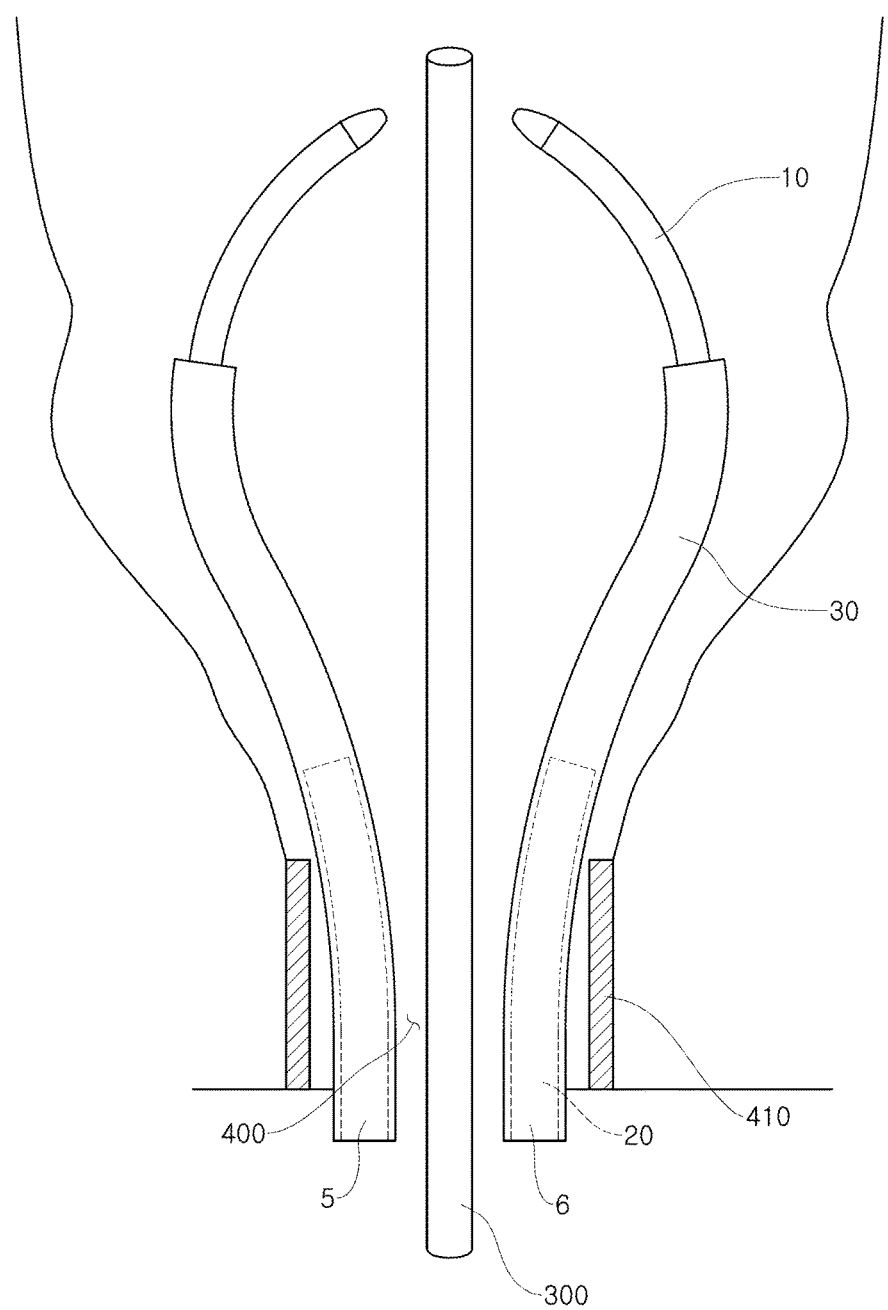
FIG. 14 is a diagram illustrating a process in which the twist of the first tube continuum and the second tube continuum is loosened.

FIGS. 12 to 14 show that a first tube continuum and a second continuum each including three tube bodies are simultaneously inserted into a task space through an entry passage to perform an operation.

First, in FIG. 12, a structure in which a plurality of tube continua 5 and 6 is simultaneously inserted into an entry passage 400 is shown. A pipe 410 is installed on the outer surface of the entry passage 400. The pipe 410 provides guidance to maintain the size of the entry passage 400. Also, the volume of the entry passage 400 gradually increases inwards.

As shown in FIG. 12, the tube continua include the first tube continuum 5 and the second tube continuum 6 having the same structure. Although this embodiment describes that two tube continua are inserted along the entry passage, the number of tube continua inserted into the entry passage is not limited thereto. Each of the first tube continuum 5 and the second tube continuum 6 includes the inner side connection tube body 10, the basic tube body 20, and the outer side connection tube body 30. Also, each of the plurality of tube continua has a spiral structure, to minimize the width of the plurality of tube continua moving along the entry passage.

In order to minimize the entrance area of the first tube continuum 5 and the second tube continuum 6 when inserting the tube continua 5 and 6 into the entry passage 400, the first tube continuum 5 and the second tube continuum 6 have a structure in which they are twisted with each other as shown in FIG. 13.

The first tube continuum 5 includes the basic straight section 21, and a first deformed section extending in front of the basic straight section 21 and having a plurality of curved sections. Hereinafter, the basic straight section 21 of the first tube continuum 5 is referred to as a first undeformed section. Likewise, the second tube continuum 6 has a second undeformed section, and a second deformed section extending in front of the second undeformed section and having a plurality of curved sections.

The first tube continuum 5 and the second tube continuum 6 are disposed spaced apart a predetermined distance from each other in a state that the tube continua are twisted with each other. Specifically, a central axis 350 extending in the lengthwise direction of the entry passage is formed at a middle point between the first deformed section and the second deformed section, and the first deformed section and the second deformed section have a structure that the deformed sections are twisted with each other by their rotation and extension in the same direction with respect to the central axis 350.

The central axis 350 is an imaginary line extending in the y axis direction from the middle point between the first tube continuum 5 and the second tube continuum 6. Here, the y axis direction refers to the lengthwise direction of the entry passage 400, that is, a direction in which the tube continua 5 and 6 are inserted into the task space through the entry passage 400.

The first undeformed section extends along the y axis parallel to the central axis 350. The basic curved section of the first tube continuum 5 is placed in front of the first undeformed section.

Also, three tube bodies 10, 20, and 30 that make up the first tube continuum 5 are rotatable or moveable back and forth independently of each other. Thus, the basic curved section of the first tube continuum 5 can rotate in the upward direction with respect to the z axis extending in the direction perpendicular to the xy plane. Also, the outer side curved section of the first tube continuum 5 placed in front of the basic curved section rotates in the downward direction with respect to the z axis. Also, the inner side curved section of the first tube continuum 5 placed in front of the outer side curved section rotates in the upward direction again.

By the rotation of each curved section, a part of the first tube continuum 5 placed in front of the basic curved section extends along the y axis while rotating in one direction with respect to the central axis 350, for example, a clockwise direction.

Likewise, the second undeformed section extends along the y axis parallel to the central axis 350. The basic curved section of the second tube continuum 6 is placed in front of the second undeformed section. The basic curved section of the second tube continuum 6 rotates in the downward direction with respect to the z axis. Also, the outer side curved section of the second tube continuum 6 placed in front of the basic curved section rotates in the upward direction. Also, the inner side curved section of the second tube continuum 6 placed in front of the outer side curved section rotates in the downward direction again.

By the rotation of each curved section, a part of the second tube continuum 6 placed in front of the second undeformed section extends along the y axis while rotating with respect to the central axis 350.

That is, by the rotation of each curved section of the first tube continuum 5 and each curved section of the second tube continuum 6, the first tube continuum 5 and the second tube continuum 6 will have a structure in which the tube continua are twisted with each other.

When viewed with respect to the xy plane, an intersection between the first tube continuum 5 and the second tube continuum 6 may be formed. Specifically, the first tube continuum 5 and the second tube continuum 6 intersect at the same point on the central axis 350. With respect to the movement path of the tube continua 5 and 6, when a point at which the first tube continuum 5 and the second tube continuum 6 first intersect is designated as a first intersection 610 and a point at which the first tube continuum 5 and the second tube continuum 6 intersect subsequent to the first intersection 610 is designated as a second intersection 620, an intersection region 630 is formed between the first intersection 610 and the second intersection 620.

With respect to the z axis perpendicular to the xy plane at the intersection region 630, the first tube continuum 5 has a positive value at the first intersection 610 and a negative value at the second intersection 620. Also, the second tube continuum 6 has a negative value at the first intersection 610 and a positive value at the second intersection 620.

Also, because the first tube continuum 5 and the second tube continuum 6 are placed spaced apart a predetermined distance from each other, a predetermined gap is formed at a space between the first tube continuum 5 and the second tube continuum 6. A camera 300 having an imaging device attached to its end may be inserted into the gap. The camera 300 may be, for example, a high definition (HD) endoscope camera.

Specifically describing with reference to FIG. 13, the camera 300 is installed between the first tube continuum 5 and the second tube continuum 6 along the central axis 350. That is, the camera 300 extends along the lengthwise direction of the entry passage 400. Thus, as shown in FIG. 14, the first tube continuum 5 and the second tube continuum 6 may have a structure in which the tube continua surround the outer surface of the camera 300.

The camera 300 may act as a visual assistant to allow detailed observation during operation with the tube continua 5 and 6 in the task space. Thus, the camera 300 exerts an appreciable effect during microsurgery such as surgery for evacuation of intracerebral hemorrhage or surgery for intracranial tumor removal.

FIG. 14 shows the location of the first tube continuum 5 and the second tube continuum 6 during operation. First, the first tube continuum 5 and the second tube continuum 6 are twisted with each other around the camera 300, and in such a state, they are moved along the lengthwise direction of the entry passage 400 and inserted into the task space where an operation is conducted.

When the movement of the tube continua 5 and 6 is completed, the inner side curved section of the first tube continuum 5 and the inner side curved section of the second tube continuum 6 are all rotated in a counterclockwise direction with respect to the y axis. The twist of the first tube continuum 5 and the second tube continuum 6 is thereby loosened at the second intersection 620.

When the above task is completed, the outer side curved section of the first tube continuum 5 and the outer side curved section of the second tube continuum 6 are all rotated in a counterclockwise direction with respect to the y axis. The twist of the first tube continuum 5 and the second tube continuum 6 is thereby loosened at the first intersection 610.

The entry passage 400 has a structure in which its volume gradually increases towards the lengthwise direction. That is, a sufficient space for performing a task for loosening the twist of the first tube continuum 5 and the second tube continuum 6 is provided within the task space.

According to the present disclosure, when the plurality of tube continua is inserted into the entry passage 400, because each of the first tube continuum 5 and the second tube continuum 6 has a spiral structure and enters the entry passage 400 in a state that they are twisted with each other, the size of an entrance for invasion may be minimized.

Also, the tube bodies of the first tube continuum 5 and the tube bodies of the second tube continuum 6 are rotatable or moveable back and forth independently of each other. Thus, after the first tube continuum 5 and the second tube continuum 6 are inserted into the entry passage 400 provided with a sufficient space, a twist loosening task may be smoothly performed. Accordingly, there is an advantage that allows the user to conduct an operation with both hands within the task space by each of the tube continua 5 and 6 having undergone the loosening task.

Also, because the camera 300 is inserted between the first tube continuum 5 and the second tube continuum 6, there is an advantage that provides a visual assistance during microsurgery.

Figure 15:
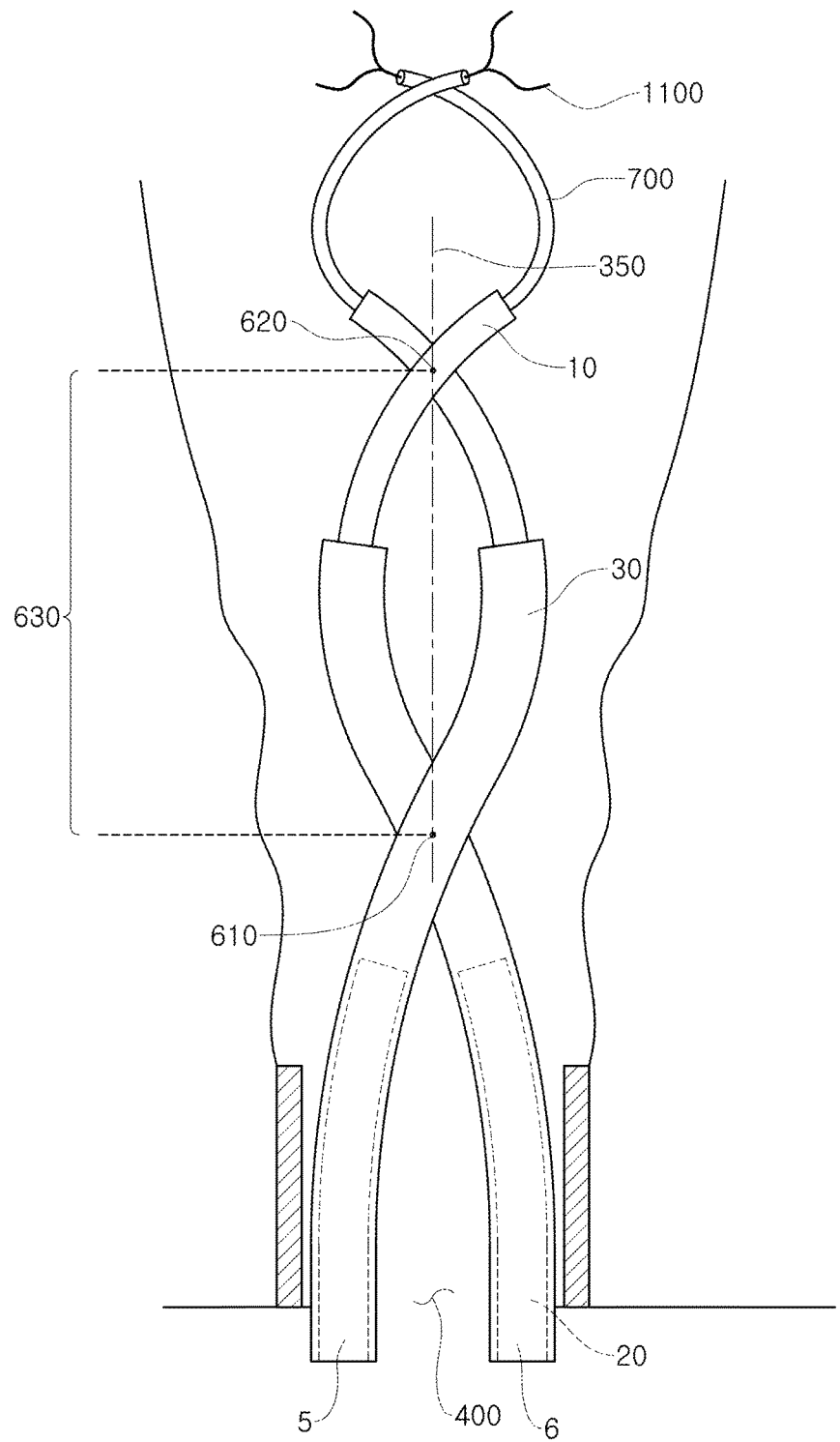
FIG. 15 is a diagram showing that a wire is inserted into each of the first tube continuum and the second tube continuum.

FIG. 15 shows that a wire is inserted into each of the first tube continuum and the second tube continuum. Specifically, a wire 700 having a smaller diameter than the inner side connection tube body 10 is inserted into the innermost space of the first tube continuum 5 and the second tube continuum 6. The wire 700 is placed in front of the inner side connection tube body 10, and the end-effector 1100 is installed at the end of the wire 700 to perform a predetermined operation task.

Also, the wire 700 is formed from a flexibly bendable material, and similar to the previous embodiment, there is an advantage that solves the control of the tube continua 5 and 6 by a linear equation.

Because each of the tube continua according to FIGS. 12 to 14 consists of three tube bodies, a total of six degrees of freedom may be achieved. However, because the tube continua according to the embodiment shown in FIG. 15 include three tube bodies and one wire 700, there is an advantage that achieves a total of eight degrees of freedom.

What is claimed is:

1. A tube continuum robot comprising:
    a basic tube body including a basic straight section extending straight, and a basic curved section extending in front of the basic straight section and bent to a predetermined curvature; and
    a connection tube body having a connection flexible section which is flexibly bendable, the connection tube body formed to be inserted into the basic tube body or to surround an exterior of the basic tube body, the connection tube body being connected with the basic tube body,
    wherein the connection flexible section has a length longer than or equal to a length of the basic curved section,
    when the basic tube body and the connection tube body are connected, the connection flexible section is placed to fully cover the basic curved section so that at least a part of the connection flexible section is bent to conform to a shape of the basic curved section,
    a front end of the connection tube body is placed at a more anterior location than a front end of the basic tube body, and
    a location and an orientation of the front end of the connection tube body is adjustable by relatively moving back and forth or rotating the basic tube body and the connection tube body.

2. The tube continuum robot according to claim 1, wherein the connection tube body comprises:
    an outer side connection tube body formed to surround the exterior of the basic tube body, the outer side connection tube body having an outer side connection flexible section which is placed to fully cover the basic curved section and bent to conform to the shape of the basic curved section; and
    an inner side connection tube body formed to be inserted into the basic tube body, the inner side connection tube body having an inner side connection flexible section which is placed to fully cover the basic curved section and bent to conform to the shape of the basic curved section, and
    each of the basic tube body, the inner side connection tube body, and the outer side connection tube body is moveable back and forth or rotatable independently.

3. The tube continuum robot according to claim 2, wherein the front end of the outer side connection tube body is placed at a more anterior location than the front end of the basic tube body, the front end of the inner side connection tube body is placed at a more anterior location than the front end of the outer side connection tube body, and the location and orientation of the front end of the inner side connection tube body is adjusted by relatively moving back and forth or rotating each of the basic tube body, the inner side connection tube body, and the outer side connection tube body.

4. The tube continuum robot according to claim 1, wherein a basic flexible section which is flexibly bendable is formed in a part or the whole of the basic tube body, and a basic guide section made from metal is installed on an outer surface of the basic flexible section at an area of overlap with the connection flexible section.

5. The tube continuum robot according to claim 3, wherein the outer side connection tube body includes an outer side straight section extending straight, and an outer side curved section extending in front of the outer side straight section and bent to a predetermined curvature, and the outer side curved section is placed at a more anterior location than the basic curved section and does not cover the basic curved section.

6. The tube continuum robot according to claim 5, wherein the outer side connection flexible section is formed in a part or the whole of the outer side curved section, and a connection guide section made from metal is installed on an outer surface of the outer side curved section having the outer side connection flexible section.

7. The tube continuum robot according to claim 5, wherein the inner side connection flexible section is formed with a length to cover both the basic curved section and the outer side curved section.

8. The tube continuum robot according to claim 5, wherein the inner side connection flexible section comprises:

a first inner side connection flexible section formed to cover the basic curved section; and a second inner side connection flexible section formed to cover the outer side curved section.

9. The tube continuum robot according to claim 5, wherein the inner side connection tube body includes an inner side straight section extending straight, and an inner side curved section extending in front of the inner side straight section and bent to a predetermined curvature, and the inner side curved section is placed at a more anterior location than the outer side curved section and does not cover the outer side curved section.

10. The tube continuum robot according to claim 3, wherein an end-effector is formed at the front end of the inner side connection tube body to perform a task within a task space into which the inner side connection tube body is inserted.

11. The tube continuum robot according to claim 5, wherein the basic tube body further includes a basic extension section extending straight in front of the basic curved section, and the outer side connection tube body further includes an outer side extension section extending straight in front of the outer side curved section.

12. A robot system for operation, comprising:

a plurality of tube continua, each tube continuum including an undeformed section extending straight, and a deformed section extending in front of the undeformed section and having a plurality of curved sections, wherein each deformed section of the plurality of tube continua is formed with a spiral structure and controllable to minimize a width of the plurality of tube continua, the plurality of tube continua enters along an entry passage in a state that the undeformed sections are arranged in parallel while the deformed sections are twisted with each other by their rotation and extension in the same direction, and when the plurality of tube continua is moved to a task space having a wider volume than the entry passage, location of ends of the deformed sections is controlled.

13. The robot system for operation according to claim 12, wherein the location of the ends of the deformed sections is controlled by moving back and forth or rotating each of the plurality of tube continua independently of each other.

14. The robot system for operation according to claim 12, wherein the deformed section comprises:

a basic curved section respectively extending in front of the undeformed section and bent to a predetermined curvature; and a connection tube body having a connection flexible section which is flexibly bendable, the connection tube body formed to be inserted into the basic curved section or to surround an exterior of the basic curved section, and a basic tube body composed of the undeformed section and the basic curved section is moveable back and forth or rotatable independently of the connection tube body.

15. The robot system for operation according to claim 14, wherein the connection tube body comprises:

an outer side connection tube body having an outer side connection flexible section which is formed to surround the exterior of the basic curved section, placed to overlap with the basic curved section, and bent to conform to a shape of the basic curved section; and an inner side connection tube body having an inner side connection flexible section which is formed to be inserted into the basic curved section, placed to overlap with the basic curved section, and bent to conform to the shape of the basic curved section, and each of the inner side connection tube body and the outer side connection tube body is moveable back and forth or rotatable independently.

16. The robot system for operation according to claim 15, wherein the outer side connection tube body includes an outer side straight section extending straight, and an outer side curved section extending in front of the outer side straight section and bent to a predetermined curvature, the inner side connection tube body includes an inner side straight section extending straight, and an inner side curved section extending in front of the inner side straight section and bent to a predetermined curvature, and when the plurality of tube continua is moved to the task space, at least one of the basic curved section, the outer side curved section, and the inner side curved section is rotated.

17. The robot system for operation according to claim 15, wherein a front end of the outer side connection tube body is placed at a more anterior location than a front end of the basic tube body, a front end of the inner side connection tube body is placed at a more anterior location than the front end of the basic tube body and a front end of the outer side connection tube body, and the tube continuum further includes a wire made from a flexibly bendable material, the wire being inserted into the inner side connection tube body.

18. The robot system for operation according to claim 12, wherein a gap extending along a lengthwise direction of the entry passage is formed between the plurality of continua, and a camera extending straight along the lengthwise direction of the entry passage is inserted into the gap.

* * * * *